United States Patent [19]
Sarantakis

[11] B 3,988,308
[45] Oct. 26, 1976

[54] (TYR³, TYR¹⁴)-SRIF AND INTERMEDIATES
[75] Inventor: Dimitrios Sarantakis, West Chester, Pa.
[73] Assignee: American Home Products Corporation, New York, N.Y.
[22] Filed: Nov. 4, 1974
[21] Appl. No.: 520,514
[44] Published under the second Trial Voluntary Protest Program on March 9, 1976 as document No. B 520,514.

[52] U.S. Cl. .......................... 260/112.5 R; 424/177
[51] Int. Cl.² .................. C07C 103/52; A61K 37/00
[58] Field of Search ................................. 260/112.5

[56] References Cited
UNITED STATES PATENTS

| | | | |
|---|---|---|---|
| 3,842,066 | 10/1974 | McKinley et al. | 260/112.5 |
| 3,842,067 | 10/1974 | Sarantakis | 260/112.5 |

*Primary Examiner*—Elbert L. Roberts
*Assistant Examiner*—Reginald J. Suyat

[57] ABSTRACT

The tetradecapeptide Ala-Gly-Tyr-Lys-Asn-Phe-Phe-Trp-Lys-Thr-Phe-Thr-Ser-Tyr-OH is described as well as novel intermediates used in the synthesis of such tetradecapeptide. This tetradecapeptide inhibits the release of growth hormone.

4 Claims, No Drawings

(TYR³, TYR¹⁴)-SRIF AND INTERMEDIATES

This invention relates to the tetradecapeptide Ala-Gly-Tyr-Lys-Asn-Phe-Phe-Trp-Lys-Thr-Phe-Thr-Ser-Tyr-OH and intermediates obtained in the synthesis of this compound.

Somatostatin (also known as somatotropin release inhibiting factor) is the tetradecapeptide H-Ala-Gly-Cys-Lys-Asn-Phe- Phe-Trp-Lys-Thr-Phe-Thr-Ser-Cys-OH.

This tetradecapeptide has only recently been identified by isolation from extracts of ovine hypothalamic tissues and found to inhibit the secretion of the hormone somatotropin which is commonly referred to as the growth hormone (GH); see Brazeau et al., Science, 179 pp 77–79 (January 1973). The linear form of this tetradecapeptide represented by H-Ala-Gly-Cys-Lys-Asn-Phe-Phe-Trp-Lys-Thr-Phe-Thr-Ser-Cys-OH, has also been reported by Brazeau et al., supra, to have been synthesized by solid phase methodology and found to have the same biological activity as the somatostatin obtained from a natural source. In U.S. Pat. No. 3,842,066 granted Oct. 15, 1974 (Ala³,Ala¹⁴)-SRIF is described as inhibiting the release of growth hormone.

The novel tetradecapeptide of the present invention is an analog of the linear counterpart of somatostatin in which the two cysteinyl amino acid residues in the three and fourteen position have been replaced by the tyrosyl amino acid residues.

The novel tetradecapeptide of the present invention is defined by the formula Ala-Gly-Tyr-Lys-Asn-Phe-Phe-Trp-Lys-Thr-Phe-Thr-Ser-Tyr-OH, (I) and non toxic acid addition salts thereof. As a convenient shorthand form this compound can be described as Tyr,$^{3,14}$-SRIF.

The nomenclature used to depict the peptides follow that described by Schroder & Lubke, "The Peptides", 1 pp viii-xxix (Academic press 1965) and in accordance with such nomenclature, it is the L form of the amino acid that is intended, unless otherwise expressly indicated.

Illustrative of pharmaceutically acceptable acid addition salts are hydrochloride, hydrobromide, sulfate, phosphate, maleate, acetate, citrate, benzoate, succinate, malate, ascorbate, and the like.

Also contemplated within the scope of the present invention are intermediates of the formula R-Ala-Gly-Tyr(R¹)-Lys(R²)-Asn-Phe-Phe-Trp-Lys(R³)-Thr(R⁴)-Phe-Thr(R⁵)-Ser(R⁶)-Tyr(R⁷)-X    II wherein: R is either hydrogen or an α-amino protecting group. The α-amino protecting groups contemplated by R are those known to be useful in the art in the step-wise synthesis of polypeptides. Among the classes of α-amino protecting groups covered by R are (1) acyl type protecting groups illustrated by the following: formyl, trifluoroacetyl, phthalyl, toluenesulfonyl (tosyl), benzensulfonyl, nitrophenylsulfenyl, tritylsulfenyl, o-nitrophenoxyacetyl, chloroacetyl, acetyl, γ-chlorobutyryl, etc.; (2) aromatic urethan type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethan protecting groups illustrated by tert-butyloxycarbonyl, diisopropylmethoxycarbonyl, isopropyloxycarbonyl, ethoxycarbonyl, allyloxycarbonyl; (4) cycloalkyl urethan type protecting groups illustrated by cyclopentyloxycarbonyl, adamantyloxycarbonyl, cyclohexyloxycarbonyl; (5) thiourethan type protecting groups such as phenylthiocarbonyl; (6) alkyl type protecting groups as illustrated by triphenylmethyl (trityl), benzyl; (7) trialkylsilane groups such as trimethylsilane. The preferred α-amino protecting group defined by R is tert-butyloxycarbonyl.

$R^1$ and $R^7$ are each a protecting group for the phenolic hydroxyl group of tyrosine selected from the group consisting of tetrahydropyranyl, tert-butyl, trityl, benzyl, 2,6-dichlorobenzyl, benzyloxycarbonyl and 4-bromobenzyloxycarbonyl. The preferred protecting group is 2,6-dichlorobenzyl or benzyl; or $R^1$ and/or $R^7$ is hydrogen which means there is no protecting group on the phenolic hydroxy function;

$R^2$ and $R^3$ are each a protecting group for the side chain amino substituent of lysine or $R^2$ and/or $R^3$ are hydrogen which means there is no protecting group on the side chain amino substituent. Illustrative of suitable side chain amino protecting groups are benzyl, chlorobenzyloxycarbonyl, benzyloxycarbonyl, tosyl, t-amyloxycarbonyl, t-butyloxycarbonyl, etc. The selection of such a side chain amino protecting group is not critical except that it must be one which is not removed during deprotection of the α-amino groups during the synthesis. Hence, the α-amino protecting and side chain amino protecting group cannot be the same;

$R^4$, $R^5$ and $R^6$ are protecting groups for the alcoholid hydroxyl group of threonine and serine and are selected from the class consisting of acetyl, benzoyl, tert-butyl, trityl, tetrahydropyranyl, benzyl, 2,6-dichlorobenzyl and benzyloxycarbonyl. The preferred protecting group is benzyl; or $R^4$ and/or $R^5$ and/or $R^6$ are hydrogen which means there is no protecting group on the alcoholic hydroxyl function;

X is selected from the class consisting of OH, $OCH_3$ and an anchoring bond used in solid phase synthesis linked to a solid resin support represented by the formula

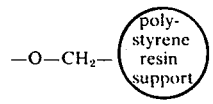

The polystyrene resin support is preferably a copolymer of styrene with about 1 to 2% divinyl benzene as a cross linking agent which causes the polystyrene polymer to be completely insoluble in certain organic solvents. The polystyrene polymer is composed of long alkyl chains bearing a phenyl ring on every second carbon and the terminal amino acid residue (Tyr) is joined through a covalent carbon to carbon bond to these phenyl rings. The alkyl chains are cross linked at approximately every fiftieth carbon by p-diethylphenyl residues derived from divinyl benzene. In formula II at least one of R, $R^1$, $R^2$, $R^3$, $R^4$, $R^5$, $R^6$ and $R^7$ is a protecting group.

In selecting a particular side chain protecting group to be used in the synthesis of the peptides of formula (I), the following rules should be followed: (a) the protecting group must be stable to the reagent and under the reaction conditions selected for removing the α-amino protecting group at each step of the synthesis, (b) the protecting group must retain its protecting properties (i.e. not be split off under coupling conditions, and (c) the side chain protecting group must be removable upon the completion of the synthesis containing the desired amino acid sequence under reaction conditions that will not alter the peptide chain.

The tetradecapeptide peptide of formula (I) is prepared using solid phase synthesis. The synthesis is commenced from the C-terminal end of the peptide using an α-amino protected resin. Such a starting material can be prepared by attaching an α-amino protected tyrosine to a chloromethylated resin or a hydroxymethyl resin. The preparation of the hydroxymethyl resin is described by Bodanszky et al., Chem. Ind (London) 38, 1597–98 (1966). A chloromethylated resin is commercially available from Bio Rad Laboratories Richmond, California and the preparation of such a resin is described by Stewart et al., "Solid Phase Peptide Synthesis" (Freeman & Co., San Francisco 1969), Chapter 1, pp 1–6. The α-amino and phenolic hydroxy protected tyrosine is coupled to the chloromethylated resin according to the procedure of Gisin, Helv. 56 p 1476 (1973). Following the coupling of the α-amino and phenolic hydroxy protected tyrosine to the resin support, the α-amino protecting group is removed such as by using trifluoroacetic acid in methylene chloride, trifluoroacetic acid along or HCl in dioxane. The deprotection is carried out at a temperature between about 0°C and room temperature. Other standard cleaving reagents and conditions for removal of specific α-amino protecting groups may be used as described in Schroder & Lubke, supra, 1 pp. 72–75. After removal of the α-amino protecting group the remaining α-amino protected amino acids are coupled step-wise in the desired order to obtain a compound of formula (I) or as an alternate to adding each amino acid separately to the synthesis, some of them may be coupled prior to addition to the solid phase reactor. Thus, the dipeptide fragments R-Thr($R^5$)-Ser($R^6$)-OH and R-Ala-Gly-OH are preferably first synthesized prior to coupling to the resin. The selection of an appropriate coupling reagent is within the skill of the art. A particularly suitable coupling reagent is $N,N^1$-diisopropyl carbodiimide. As previously indicated, the activating reagents used in the aforedescribed synthesis are those well known in the peptide art. Illustrative of these are: (1) carbodiimides (e.g. $N,N^1$-dicyclohexycarbodiimide, N-ethyl $N^1$-(γ-dimethylamino propyl carbodiimide); (2) cyanamides (e.g. N,N-dibenzylcyanamide; (3) keteimines; (4) isoxazolium salts (e.g. N-ethyl-5-phenyl isoxazolium-$3^1$-sulfonate; (5) monocyclic nitrogen containing heterocyclic amides of aromatic character containing one through four nitrogens in the ring such as imidazolides, pyrazolides, 1,2,4-triazolides. Specific heterocyclic amides that are useful include $N,N^1$-carbonyl diimidazole, $N,N^1$-carbonyl-di-1,2,4-triazole; (6) alkoxylated acetylene (e.g. ethoxyacetylene); (7) reagents which form a mixed anhydride with the carboxyl moiety of the amino acid (e.g. ethylchloroformate, isobutylchloroformate) and (8) nitrogen-containing heterocyclic compounds having a hydroxy group on one ring nitrogen (e.g. N-hydroxyphthalimide, N-hydroxysuccinimide, 1-hydroxybenzotriazole). Other activating reagents and their use in peptide coupling are described by Schroder & Lubke supra, in Chapter III and by Kapoor, J. Pharm. Sci., 59, pp 1–27, (1970). It has been found desirable to add the R-Thr($R^5$)-Ser($R^6$)-OH fragments to the resin in the presence of N-hydroxybenzotriazole in order to minimize racemization.

Each protected amino acid or amino acid sequence is introduced into the solid phase reactor in about a four-fold excess and the coupling is carried out in a medium of dimethylformamide: methylene chloride (1:1) or in dimethylformamide or methylene chloride alone. In cases where incomplete coupling occurred the coupling procedure is repeated before removal of the α-amino protecting group, prior to the coupling of the next amino acid to the solid phase reactor. The success of the coupling reaction at each stage of the synthesis is monitored by the ninhydrin reaction as described by E. Kaiser et al., Analyt. Biochem, 34, 595 (1970).

After the desired amino acid sequence of formula II has been synthesized, the peptide is removed from the resin support by treatment with a reagent such as liquid hydrogen fluoride which not only cleaves the peptide from the resin but also cleaves all remaining side chain protecting groups $R^1$, $R^2$, $R^3$, $R^4$, $R^5$, $R^6$ and $R^7$ and the α-amino protecting group R on tyrosine to obtain directly a compound of formula I. As an alternate route, the tetradecapeptide linked to the resin support may be separated from the resin by methanolysis after which the recovered C-terminal methyl ester is converted to the acid by hydrolysis. Any side chain protecting group may then be cleaved as previously described or by other procedures such as catalytic reduction (e.g. Pd on $BsSO_4$) using conditions which will keep the Trp moiety intact. When using hydrogen fluoride for cleaving, anisole is included in the reaction vessel to prevent the oxidation of labile amino acid (e.g. tryptophan).

The solid phase synthesis procedure discussed supra is well known in the art and has been essentially described by Merrifield J. Am. Chem. Soc., 85, p 2149 (1964).

The following examples are illustrative of the preparation of the compounds of formulas I and II.

EXAMPLE 1 t-Butyloxycarbonyl-L-alanylglycyl-O-2,6-dichlorobenzyl-L-tyrosyl-N -2-chlorobenzyloxycarbonyl-L-lysyl-L-asparaginyl-L-phenylalanyl-L-phenylalanyl-L-tryptophyl-N -2-chlorobenzyloxycarbonyl-L-lysyl-O-benzyl-L-threonyl-L-phenylalanyl-O-benzyl-L-threonyl-O-benzyl-L-seryl-O-2,6-dichlorobenzyl-L-tyrosyl methylated polystyrene resin Chloromethylated polystyrene resin (6 g) is stirred in a pressure bottle at 50°C for 16 hours with the cesium salt of t-butyloxycarbonyl-O-2,6-dichlorobenzyl-L-tyrosine (2.87 g, 5 m mmoles) in dimethylformamide (45 mg). The resin is filtered and washed on the filter with dimethylformamide, 9:1 dimethylformamide/water, 1:1 ethanol/dimethylformamide, dimethylformamide, and methylene chloride. The resin is found to be substituted to the extent of 0.41 m mole of tyrosine per gram of resin.

The resin is transferred to a reaction vessel (10 g capacity) of the Beckman 990 peptide synthesizer and deprotected and neutralized as follows: the resin is treated with two portions of 1:1 trifluoroacetic acid and methylene chloride containing 5% ethanedithiol for a total of 35 minutes, then washed with methylene chloride six times allowing a contact time of 3 minutes for each wash. Neutralization is carried out with three treatments with 12.5% triethylamine in dimethylformamide for a total of 9 minutes, then washing with methylene chloride six times again for 3 minutes each.

All the couplings are carried out two times using 4 m moles of protected amino acid each time and a 10% excess of diisopropylcarbodiimide as coupling reagent allowing two hours for each coupling. Asparagine is the only exception; it is coupled as the p-nitrophenyl ester with a catalytic amount of acetic acid allowing 10 hours for each coupling. After the second coupling reaction of each amino acid and before deprotecting, the peptide resin is acetylated with 2.5% acetylimidazole in methylene chloride for 30 minutes. Washings with methylene chloride and dimethylformamide are carried out between and after couplings and acetylations. The following amino acid and dipeptide residues are introduced consecutively: t-Boc-O-benzyl-L-threonyl-O-benzyl-L-serine, t-Boc-L-phenylalanine, t-Boc-O-benzyl-L-threonine, t-Boc-N -(2-chlorobenzyloxycarbonyl)-L-lysine, t-Boc-L-tryptophan, t-Boc-L-phenylalanine, t-Boc-L-phenylalanine, t-Boc-L-asparagine p-nitrophenyl ester, t-Boc-N -(2-chlorobenzyloxycarbonyl)-L-lysine, t-Boc-O-(2,6-dichlorobenzyl)-L-tyrosine and t-Boc-L-alanylglycine to yield the above titled product.

The t-Boc-O-benzyl-L-threonyl-O-benzyl-L-serine and t-Boc-L-alanylglycine used in this Example were prepared by the procedure described in Examples I, IV and V of copending application Ser. No. 376,472 filed July 5, 1972, the disclosure of which is incorporated herein by reference.

EXAMPLE 2

L-Alanylglycyl-L-tyrosyl-L-lysyl-L-asparaginyl-L-phenylalanyl-L-phenylalanyl-L-tryptophyl-L-lysyl-L-threonyl-L-phenylalanyl-L-threonyl-L-seryl-L-tyrosine The above described preparation obtained in Example 1 is treated in vacuo with liquid anhydrous hydrogen fluoride (50 ml) and anisole (15 ml) at ambient temperature for 45 minutes. The hydrogen fluoride and anisole are then removed as quickly as possible under reduced pressure and the residue washed with ether. The product is then taken up in 2 N acetic acid, filtered from the resin, and lyophilized to leave the above titled product (3.33 g).

EXAMPLE 3 Purification and characterization of L-alanylglycyl-L-tyrosyl-L-lysyl-L-asparaginyl-L-phenylalanyl-L-phenylalanyl-L-tryptophyl-L-lysyl-L-threonyl-L-phenylalanyl-L-threonyl-L-seryl-L-tyrosine The above titled crude product obtained in Example 2 is purified as follows: 3.33 g of this product in a small volume of the upper phase of n-butanol:water:acetic acid 4:5:1 is applied to a column (2.9 cm in diameter and 150 cm in height) with a bed of Sephadex G-25 medium previously equilibrated with first the lower phase of that system and then the upper phase. The column is eluted with the upper phase and fractions of 5 ml each are taken. The column effluent is monitored by use of the Folin-Lowry color reaction on every third fraction. Seven peptide containing fractions are obtained, a) tubes 65–80 (563 mg), b) tubes 81–95 (536 mg), c) tubes 96–110 (438 mg), d) tubes 111–130 (424 mg), e) tubes 131–150 (317 mg), f) tubes 151–170 (223 mg), g) tubes 171–190 (135 mg). Fractions B and C (974 mg) are shown by thin layer chromatography system BWA 4:1:1 (n-butanol:water:acetic acid) on cellulose to be the purest. They are combined and applied in a small volume of 2 N acetic acid to a column (2.5 cm in diameter and 150 cm in height) with a bed of Sephadex G-25 fine previously equilibrated with 2 N acetic acid. The column is eluted with that solvent and fractions of 3 ml each are taken. The effluent is monitored as described before. Five peptide containing fractions are obtained, $\alpha$) tubes 70–85 (263 mg), A) tubes 86–95 (157 mg), B) tubes 96–105 (200 mg), C) tubes 106–115 (152 mg), D) tubes 116–125 (75 mg). Fractions A–C (509 mg) are the purest as indicated by thin layer chromatography system BWA 4:1:1 on cellulose. They are combined and applied in a small volume of 2 N acetic acid to a column (2.5 cm in diameter and 150 cm in height) with a bed of Sephadex G-25 fine previously equilibrated with 2 N acetic acid. The column is eluted with that solvent and fractions of 3 ml each are taken. The effluent is monitored as before. Four peptide containing fractions are obtained, A) tubes 84–95 (84 mg), B) tubes 96–105 (104 mg), C) tubes 106–115 (84 mg), D) tubes 116–130 (71 mg). Fraction A is homogenous on thin layer chromatography systems BWA 4:1:1 on cellulose and BWAP 4:2:1:1 (n-butanol:water: acetic acid:pyridine) on silica gel. Thin layer chromatograms are visualized with chlorine peptide reagent; $[\alpha]_D^{26} = -25.46$ (c= 0.982, 1% AcOH).

After hydrolysis of the peptide for 24 hours in methanesulfonic acid at 110°C in an evacuated sealed tube, the following values for $Tyr^{3,14}$-SRIF are obtained: Ala 0.97; Gly 1.00; Tyr 1.94; Lys 2.02; Asp 1.02, Phe 3.17; Trp 0.71; Thr 1.67; Ser 0.60.

The growth hormone inhibiting activity of the compound of Example 3 was determined by radioimmunoassay in a rat pituitary cell culture system as described by Vale et al, Endocrinology 91, pp 562 (1972) and Grant et al, Biochemical and Biophysical Research Communications 51, pp 100–106 (1973). The compound of Example 3 was tested at 10 ng/ml, 100 ng/ml and 1000ng/ml and was active at these concentrations in inhibiting growth hormone release. The in vivo activity of the compound of Example 3 was determined by dissolving 500 $\mu$g of this compound in a mixture of polyethylene glycol (PEG 400) and water (1 ml) and the mixture was injected in rats weighing 200–240 g. Control rats were injected with 80% PEG 400. One hour and forty minutes later the rats were injected i.p. with nembutal at 50 mg/kg. Twenty minutes after the nembutal injection the rats were killed and their blood plasmas were assayed for growth hormone by radioimmunoassay.

The average of 19 treated rats was $80.1 \pm 9.0 \times 10^{-9}$g GH/ml and the average of 11 control rats was $117.9 \pm 13.6 \times 10^{-9}$g GH/ml.

The compounds described herein may be administered to warm blooded mammals, including humans, either intravenously, subcutaneously, intramuscularly or orally to inhibit the release of growth hormone where the host being treated requires therapeutic treatment for excess secretion of somatotropin which is associated with conditions such as juvenile diabetes and acromegaly. The contemplated dose range for oral administration in tablet or capsule form to large mammals is about 0.015 mg to about 7 mg/kg of body weight per day while the dose range for intravenous injection in an aqueous solution is about 0.1 $\mu$g to about 0.15 mg/kg of body weight per day. When administered subcutaneously or intramuscularly a dose range of about 1.5 $\mu$g to about 0.7 mg/kg of body weight per day is contemplated. Obviously, the required dosage will vary with the particular condition being treated, the severity of the condition and the duration of treatment.

If the active ingredient is administered in tablet form the tablet may contain: a binder such as gum tragacanth, corn starch, gelatin, an excipient such as dicalcium phosphate; a disintegrating agent such as corn starch, alginic acid, etc.; a lubricant such as magnesium stearate; and a sweetening and/or flavoring agent such as sucrose, lactose, wintergreen, etc. Suitable liquid carriers for intravenous administration include isotonic saline; phosphate buffer solutions, etc.

What is claimed is:

1. A compound selected from those of the formula:

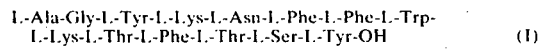

and

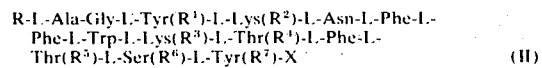

and the non-toxic salts thereof, wherein:

R is selected from the class consisting of H and an α-amino protecting group;

$R^1$ and $R^7$ are selected from the class consisting of hydrogen and a protecting group for the phenolic hydroxyl group of tyrosine selected from tetrahydropyranyl, tert-butyl, trityl, benzyl, 2,6-dichlorobenzyl, benzyloxycarbonyl and 4-bromobenzyloxycarbonyl;

$R^2$ and $R^3$ are selected from the class consisting of hydrogen and a side chain amino protecting group;

$R^4$, $R^5$ and $R^6$ are selected from the class consisting of hydrogen and a protecting group for the alcoholic group selected from acetyl, benzoyl, tert-butyl, trityl, benzyl and benzyloxycarbonyl; with the proviso that at least one of R, $R^1$, $R^2$, $R^3$, $R^4$, $R^5$, $R^6$ and $R^7$ is other than hydrogen;

X is selected from the class consisting of hydroxy, methoxy and

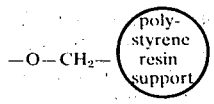

wherein said polystyrene is cross linked through the phenyl group on each second carbon atom of the alkyl chain of said polystyrene.

2. A compound according to claim 1 which is selected from L-alanylglycyl-L-tyrosyl-L-lysyl-L-asparaginyl-L-phenylalanyl-L-phenylalanyl-L-tryptophyl-L-lysyl-L-threonyl-L-phenylalanyl-L-threonyl-L-seryl-L-tyrosine and its non-toxic acid addition salts.

3. A compound represented by formula II of claim 1, wherein X is

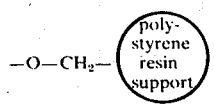

4. a compound according to claim 3 wherein R is tert-butyl-oxycarbonyl and each of $R^4$, $R^5$ and $R^6$ are benzyl, $R^2$ and $R^3$ are 2-chlorobenzyloxycarbonyl and $R^1$ and $R^7$ are 2,6-dichlorobenzyl.

* * * * *